(12) United States Patent
Hashimoto

(10) Patent No.: US 8,466,957 B2
(45) Date of Patent: Jun. 18, 2013

(54) ENDOSCOPE AND ENDOSCOPE APPARATUS

(75) Inventor: Hidenori Hashimoto, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/437,109

(22) Filed: Apr. 2, 2012

(65) Prior Publication Data

US 2012/0249763 A1 Oct. 4, 2012

Related U.S. Application Data

(63) Continuation of application No. PCT/JP2011/063697, filed on Jun. 15, 2011.

(30) Foreign Application Priority Data

Sep. 13, 2010 (JP) ................................. 2010-204560

(51) Int. Cl.
*H04N 7/18* (2006.01)
(52) U.S. Cl.
USPC ............................................. 348/65; 348/61

(58) Field of Classification Search
USPC ...................................................... 348/61, 65
See application file for complete search history.

(56) References Cited

U.S. PATENT DOCUMENTS

2008/0183981 A1 7/2008 Tannai

FOREIGN PATENT DOCUMENTS

| JP | 2000-254093 | 9/2000 |
|---|---|---|
| JP | 2004-305373 | 11/2004 |
| JP | 2008-104535 | 5/2008 |
| JP | 2008-229208 | 10/2008 |

*Primary Examiner* — Allen Wong
(74) *Attorney, Agent, or Firm* — Scully, Scott, Murphy & Presser, P.C.

(57) ABSTRACT

An endoscope includes: a CCD that picks up an image of a subject; an FPGA that is controlled by a main body portion 3 to output a drive signal for driving the CCD and transmits an image pickup signal outputted from the CCD to the main body; rewritable flash memory in which at least one of program data and setting data that relate to an operation of the FPGA is stored; and a switch group that, based on a rewriting instruction signal SW to the data in the flash memory, switches so that the data received by using all or a part of signal lines for the CCD, the lines being associated with observation of the subject, is inputted to the flash memory.

11 Claims, 3 Drawing Sheets

ENDOSCOPE AND ENDOSCOPE APPARATUS

CROSS REFERENCE TO RELATED APPLICATION

This application is a continuation application of PCT/JP2011/063697 filed on Jun. 15, 2011 and claims benefit of Japanese Application No. 2010-204560 filed in Japan on Sep. 13, 2010, the entire contents of which are incorporated herein by this reference.

BACKGROUND OF THE INVENTION

1. Field of the Invention

The present invention relates to an endoscope and an endoscope apparatus.

2. Description of the Related Art

Conventionally, endoscope apparatuses have been widely used in a medical field and an industrial field. Generally, an endoscope apparatus includes an endoscope with an elongated insertion portion and a main body portion connected with the endoscope. The main body portion receives image signals from an image pickup device provided at a distal end of the insertion portion and displays an image on a monitor.

In order to reduce a number of signal lines between an endoscope and a main body portion, as disclosed in Japanese Patent Application Laid-Open Publication No. 2004-305373 and Japanese Patent Application Laid-Open Publication No. 2008-229208, an endoscope apparatus has been proposed that time division multiplexes video signals from a scope and outputs resultant signals to a processor.

Also, conventionally, there are endoscope apparatuses that have a plurality of modes. Examples of the modes include a normal observation mode for observation performed to examine a subject and a mode for rewriting data of rewritable non-volatile memory in an endoscope.

SUMMARY OF THE INVENTION

An endoscope according to an aspect of the present invention is an endoscope connectable to an outside apparatus, the endoscope including: an image pickup device that picks up an image of a subject; an image pickup control portion that is controlled by the outside apparatus to output a drive signal for driving the image pickup device and transmits an image pickup signal outputted from the image pickup device to the outside apparatus; a rewritable storage portion in which at least one of program data and setting data that relate to an operation of the image pickup control portion is stored; and a switching control portion that, based on a rewriting instruction signal of the at least one data in the storage portion, switches so that the at least one data received by using all or a part of signal lines for the image pickup device, the lines being provided to connect the outside apparatus to the endoscope and associated with observation of the subject, is inputted to the storage portion.

An endoscope apparatus according to an aspect of the present invention is an endoscope apparatus including an outside apparatus and an endoscope connectable to the outside apparatus via a cable, wherein the endoscope includes: an image pickup device that picks up an image of a subject; an image pickup control portion that is controlled by the outside apparatus to output a drive signal for driving the image pickup device and transmits a signal obtained by processing an image pickup signal outputted from the image pickup device to the outside apparatus; a rewritable storage portion in which at least one of program data and setting data that relate to an operation of the image pickup control portion is stored; and a switching control portion that, based on a rewriting instruction signal of the at least one data in the storage portion, switches so that the at least one data received by using all or a part of signal lines included in the cable for the image pickup device, the lines being associated with observation of the subject, is inputted to the storage portion.

DETAILED DESCRIPTION OF THE PREFERRED EMBODIMENT

An embodiment of the present invention will now be described with reference to the drawings.
(Configuration)

Figure 1:
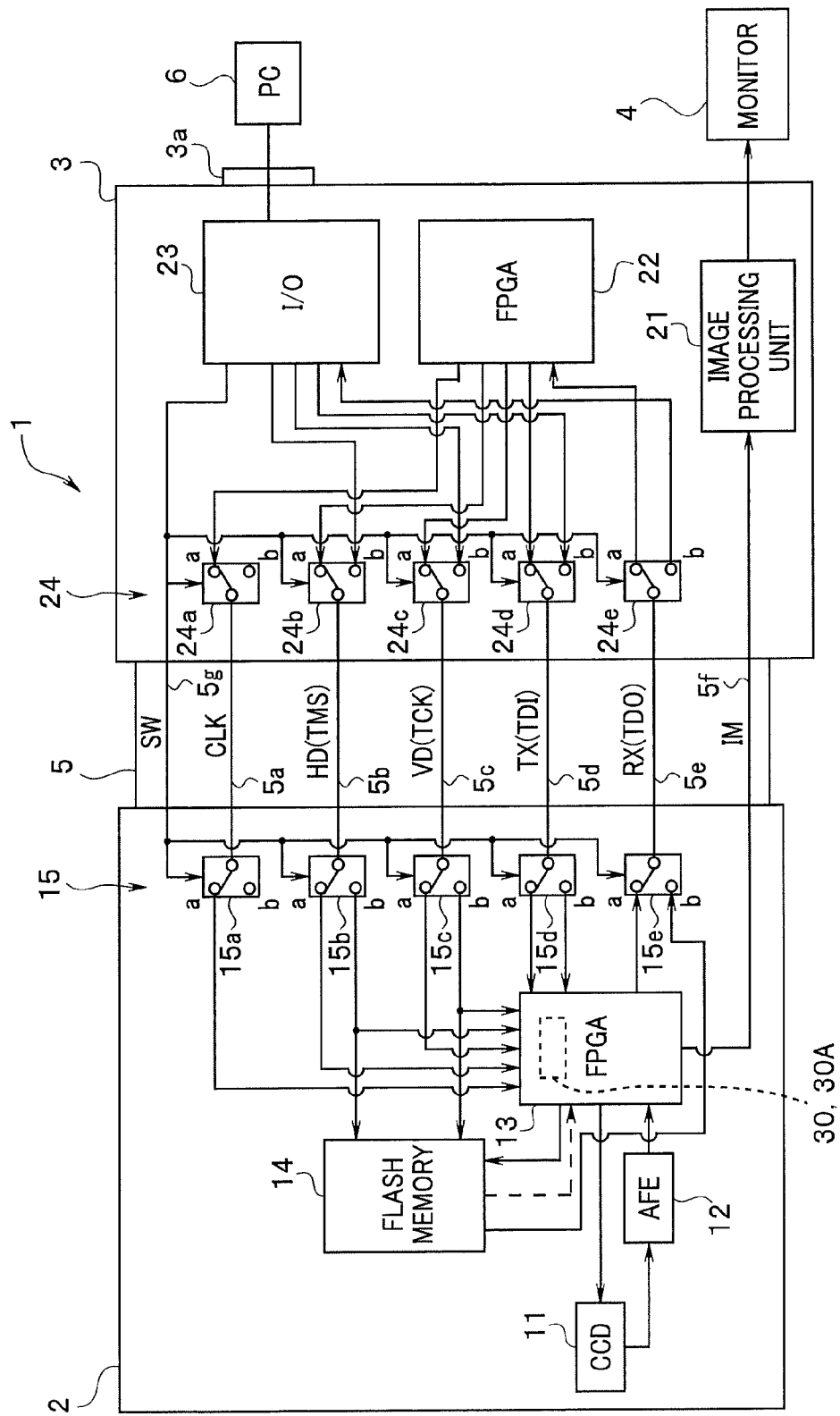
FIG. 1 is a block diagram illustrating a configuration of an endoscope apparatus in accordance with an embodiment of the present invention.

First, a configuration of an endoscope apparatus according to the present embodiment will be described with reference to FIG. 1. FIG. 1 is a block diagram illustrating the configuration of the endoscope apparatus according to the present embodiment.

An endoscope apparatus 1 includes an endoscope 2, a main body portion 3, and a monitor 4. The endoscope 2 is connectable to the main body portion 3, which is an outside apparatus, and the endoscope 2 and the main body portion 3 is connected with each other through a cable 5 including a plurality of signal lines. A personal computer (hereinafter, referred to as a PC) 6 that is an outside apparatus is also connectable to the main body portion 3 through a connector 3a of the main body portion 3. The monitor 4 is connected with the main body portion 3.

The endoscope apparatus 1 has, as operation modes, an observation mode for observing an inside of a subject, a data writing mode for rewriting data in the endoscope 2, and a unit test mode for testing each unit in the endoscope 2. A user can operate an operation portion (not shown) of the main body portion 3 to choose and change one of the operation modes of the endoscope apparatus 1.

The endoscope 2 includes a CCD 11 that is an image pickup device for picking up an image of a subject, an analog front end (AFE) portion 12 including an analog-digital conversion circuit and a correlated double sampling circuit, an FPGA (Field Programmable Gate Array) 13 that is an image pickup control portion, a flash memory 14 that is rewritable non-volatile memory, and a switch group 15 composed of five switches 15a to 15e. It should be noted that in FIG. 1, an objective lens for the CCD 11, a bending portion, and the like are omitted, so that they are not shown.

The CCD 11 is provided at a distal end portion of an insertion portion of the endoscope 2 and installed so that an image pickup surface is positioned at a focal position of an objective optical system, which is not shown. The analog front end portion 12 eliminates a noise in image pickup signals received from the CCD 11 and outputs the image pickup signals to the FPGA 13.

The FPGA 13 receives a drive signal and a control signal from outside to generate and output a drive signal and a control signal to the CCD 11, and to receive from the analog front end portion 12 and output an image signal. Also, the FPGA 13 is a programmable device, an internal configuration of which can be changed based on configuration data. The FPGA 13 constitutes an image pickup control portion that is controlled by the main body portion 3 to output a drive signal for driving the CCD 11 and transmits an image pickup signal outputted from the CCD 11 to the main body portion 3.

Specifically, in the observation mode for observing a subject, the FPGA 13 as the image pickup control portion generates and outputs drive signals to the CCD 11 based on clock signals CLK, horizontal synchronizing signals HD and vertical synchronizing signals VD from the main body portion 3, while the FPGA 13 receives image signals from the CCD 11 and transmits the signals to the main body portion 3. Further, the FPGA 13 executes various types of control processing such as shutter speed control for the CCD 11 based on various types of control data from the main body portion 3.

On the other hand, in the data writing mode and the unit test mode, the FPGA 13 executes processing for receiving data and transferring the data to the flash memory 14.

In the flash memory 14, configuration data for the FPGA 13, which is the image pickup control portion, and various types of setting data needed for image pickup are stored. When being activated, the endoscope 2 first uses the configuration data stored in the flash memory 14 to configure the FPGA 13. The configuration data is program data for providing various functions of the endoscope 2 and defining an internal configuration of the FPGA 13.

Specifically, once the endoscope apparatus 1 is powered on, in the endoscope 2, the configuration data stored in the flash memory 14 is read out and written in the FPGA 13, and the FPGA 13 is configured based on the written configuration data. For example, upgrading the endoscope 2 may also be accomplished by rewriting the configuration data.

Also, the various types of setting data are, for example, various adjustment parameters used in the observation mode. Thus, the flash memory 14 is a rewritable storage portion in which one of the program data and the setting data that relate to an operation of an image pickup section is stored.

The configuration data and the setting data are rewritten, as described later, by writing new configuration data or new setting data into the flash memory 14 of the endoscope 2 through the main body portion 3 from the PC 6 connected with the main body portion 3. Alternatively, a function to rewrite the configuration data and the setting data may be provided in the main body portion 3, and the main body portion 3 may rewrite the configuration data and the setting data.

The main body portion 3, which is an outside apparatus, includes an image processing unit 21 that receives and processes image signals from the endoscope 2, an FPGA 22 that is a control portion, an interface portion (hereinafter, referred to as the I/O portion) 23 with the PC 6, and a switch group 24 composed of five switches 24a to 24e. It should be noted that in FIG. 1, an operation portion operated by a user, a light source control portion and the like are omitted and not shown. The image processing unit 21 processes image signals IM from the endoscope 2 to generate and output signals for displaying on the monitor 4 video of a subject obtained by the CCD 11 picking up an image.

The FPGA 22 performs processing such as generating and outputting clock signals CLK, horizontal synchronizing signals HD, vertical synchronizing signals VD, and control signals TX to be supplied to the endoscope 2, and receiving control signals RX. Further, the FPGA 22 also controls the operation portion of the main body portion 3 and the like.

The I/O portion 23 is an interface circuit with the PC 6, and transmits and receives between the PC 6 and the endoscope 2 various signals for processing in the data writing mode and processing in the unit test mode, which are described later.

As described above, the endoscope 2 and the main body portion 3 are connected with each other through the cable 5 including a plurality of signal lines, but in FIG. 1, a power line and a ground line are omitted.

Next, connection between each signal line and each switch will be described. Five switches 5a to 5e are provided in the endoscope 2, and the five switches 24a to 24e are provided in the main body portion 3. Each switch is switched based on a mode switching signal SW from the main body portion 3.

A signal line 5a connects the switches 15a and 24a to each other, a signal line 5b connects the switches 15b and 24b to each other, a signal line 5c connects the switches 15c and 24c to each other, a signal line 5d connects the switches 15d and 24d to each other, and a signal line 5e connects the switches 15e and 24e to each other. A signal line 5f connects the FPGA 13 and the image processing unit 21 to each other so as to supply the image signals IM from the FPGA 13 of the endoscope 2 to the image processing unit 21 of the main body portion 3.

The mode switching signals SW are supplied to each switch from the PC 6 through the I/O portion 23. A signal line 5g for supplying the mode switching signals SW to the switches 15a to 15e is provided in the cable 5. From a viewpoint of the endoscope 2, the PC 6 is also an outside apparatus connected to the endoscope 2.

In the observation mode, each switch selects an a-side in FIG. 1, so that various signals from the FPGA 22 in the main body portion 3 are supplied to the FPGA 13 in the endoscope 2, and control signals from the FPGA 13 in the endoscope 2 are supplied to the FPGA 22 of the main body portion 3.

Specifically, the clock signals CLK from the FPGA 22 are supplied to the FPGA 13 via the switch 24a, the signal line 5a, and the switch 15a. The horizontal synchronizing signals HD are supplied to the FPGA 13 via the switch 24b, the signal line 5b, and the switch 15b. The vertical synchronizing signals VD are supplied to the FPGA 13 via the switch 24c, the signal line 5c, and the switch 15c. Also, the control signals TX from the FPGA 22 to the FPGA 13 are supplied via the switch 24d, the signal line 5d, and the switch 15d, and the control signals RX from the FPGA 13 to the FPGA 22 are supplied via the switch 15e, the signal line 5e, and the switch 24e.

Then, the image signals IM processed by the analog front end portion 12 and the FPGA 13 are supplied to the image processing unit 21 via the signal line 5f; and as a result, an endoscope image is displayed on the monitor 4.

In the data writing mode, each switch selects a b-side in FIG. 1 based on the mode switching signals SW, so that various signals from the I/O 23 in the main body portion 3 are supplied to the FPGA 13 and the flash memory 14 in the endoscope 2, and signals from the flash memory 14 are supplied to the I/O 23 of the main body portion 3.

In the present embodiment, writing data into the flash memory 14 is performed using communications conforming to a JTAG (Joint Test Action Group) standard, which is a debugging serial interface. When writing data into the flash memory 14 of the endoscope 2, the PC 6 generates signals according to a communication procedure based on the JTAG standard, and transmits through the I/O 23 to the endoscope 2 the various signals and data to be written in the flash memory 14. Here, the FPGA 13 and the flash memory 14 are connected to a chain of JTAG.

Specifically, the switches of the switch groups 15 and 24 switches to the b-side based on the mode switching signals SW. As a result, test mode selecting signals (hereinafter, referred to as TMS signals) from the PC 6 are supplied to the FPGA 13 and the flash memory 14 through the switch 24b, the signal line 5b and the switch 15b. Test clock signals (hereinafter, referred to as TCK signals) are supplied to the FPGA 13 and the flash memory 14 through the switch 24c, the signal line 5c and the switch 15c. Also, test data-in signals (hereinafter, referred to as TDI signals) from the PC 6 are supplied to the FPGA 13 through the switch 24d, the signal line 5d and the switch 15d. Test data-out signals (hereinafter, referred to as TDO signals) from the flash memory 14 are supplied to the PC 6 through the switch 15e, the signal line 5e, the switch 24e and the I/O portion 23.

Since nothing is connected to the b-side of the switches 15a and 24a, the signal line 5a does not transmit any signal. This is because the clock CLK is not used in the data writing mode (and the unit test mode).

That is, write data into the flash memory 14 is included in the TDI signals, and the data in the TDI signals is written into the flash memory 14 through the FPGA 13.

It should be noted that in the described example, the mode switching signals SW are supplied to the switches 15a to 15e of the endoscope 2 using the dedicated signal line 5g, but without providing the dedicated signal line, mode switching signals may be included in TDI signals on another signal line, e.g., the signal line 5e, and the switches 15a to 15e may be switched based on the mode switching signals.

To the FPGA 13 and the flash memory 14, the TMS signals as chip select signals and the TCK signals as operation clock signals are inputted, and data included in the TDI signals, i.e., configuration data or setting data, is written in the flash memory 14 through the FPGA 13. TDO signals according to the JTAG standard are outputted from the flash memory 14 to the PC 6 through the switch 15e, the signal line 5e, the switch 24e, and the I/O portion 23.

That is, the switch group 15 constitutes a switching control portion that, based on a rewriting instruction signal SW for the data in the flash memory 14, switches so that signals received by using all or a part of the signal lines 5a to 5e for the CCD 11, associated with observation of a subject, are inputted to the flash memory 14. Some switches of the switch group 15 constitute a plurality of switches for switching connection to the FPGA 13, of all or a part of the signal lines 5a to 5e associated with the observation, to connection to the flash memory 13.

As described above, once the endoscope 2 is activated, the configuration data of the data stored in the flash memory 14 is written in the FPGA 13 via a signal line indicated by a dotted line in FIG. 1, and the FPGA 13 is configured.

In the unit test mode for an inner circuit of the endoscope 2, the switches select the b-side in FIG. 1 based on the mode switching signals SW, and in accordance with the JTAG standard, TCK signals and TMS signals from the I/O portion 23 in the main body portion 3 are supplied to the flash memory 14 and the FPGA 14 in the endoscope 2. Then, TDI signals for, e.g., a boundary scan test of the inner circuit are supplied to the FPGA 13, and TDO signals are outputted from the flash memory 14 and supplied to the I/O 23 of the main body portion 3.

It should be noted that in FIG. 1, in the example of the test mode according to the JTAG standard, two circuits of the flash memory 12 and the FPGA 13 are tested, but the CCD 11 and the analog front end portion 12 may also be included in a chain of JTAG, and a boundary scan test according to JTAG may be carried out thereon.

The unit test mode tests the inner circuit in the endoscope 2, and here, a unit including the FPGA 13 and a unit including the flash memory 14 are tested. Thus, determination of which of the units is out of order can be made based on a test result.

As described above, if an image pickup unit including the CCD 11 is also included in the chain of JTAG as well as a unit of the operation portion, a unit of the connector portion, and the like are included in the chain of JTAG, determination can be made of which of the units in the endoscope 2, e.g., the image pickup unit, the operation portion, the connector portion, or the like is out of order.

Also, the unit test mode may additionally be provided with a special test mode. For example, predetermined image data for test is stored beforehand in the flash memory 14, and the predetermined image data is read out in the test mode and transmitted from the endoscope 2 to the main body portion 3. In the main body portion 3, a quality of signals on a channel for image signals can be checked by checking whether or not received image data has been properly received. As described above, in the observation mode, the CCD 11 operates based on drive signals and control signals from the FPGA 13, and in the data writing mode, data from the outside apparatus is written in the flash memory 14 using a part of the plurality of signal lines used in the observation mode, for the drive signals and the control signals.

Furthermore, in the data writing mode and the unit test mode, since the JTAG standard, which is one of debugging serial interfaces, is used to transmit/receive data, data and test signals are supplied from the outside apparatus, so that data is written in the endoscope 2 and the endoscope is tested.

Figure 2:
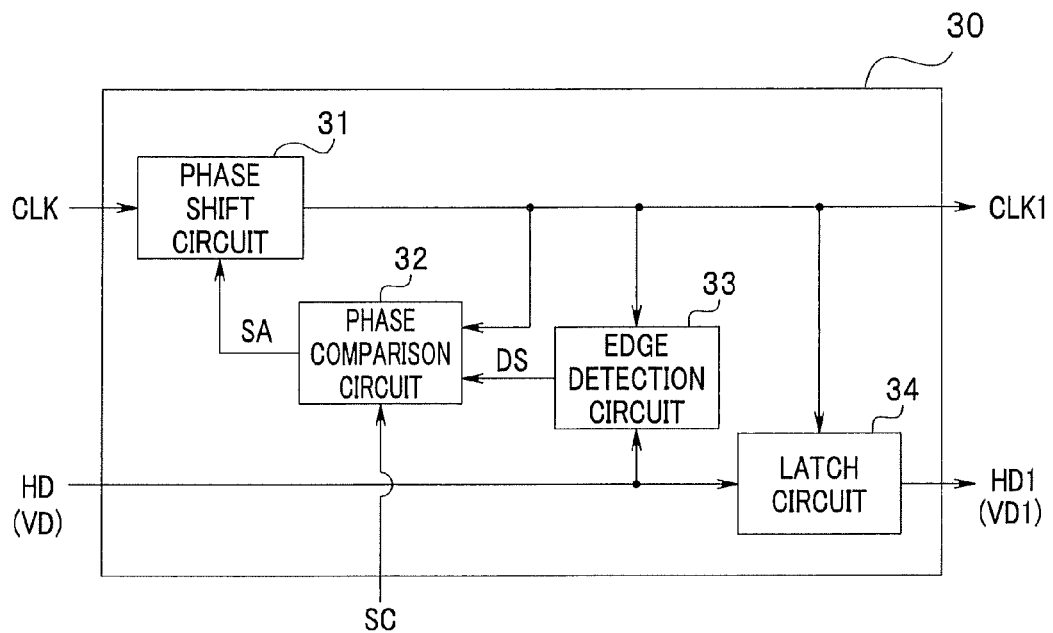
FIG. 2 is a diagram illustrating an example of an out-of-synchronization prevention circuit in accordance with the embodiment of the present invention.
Figure 3:
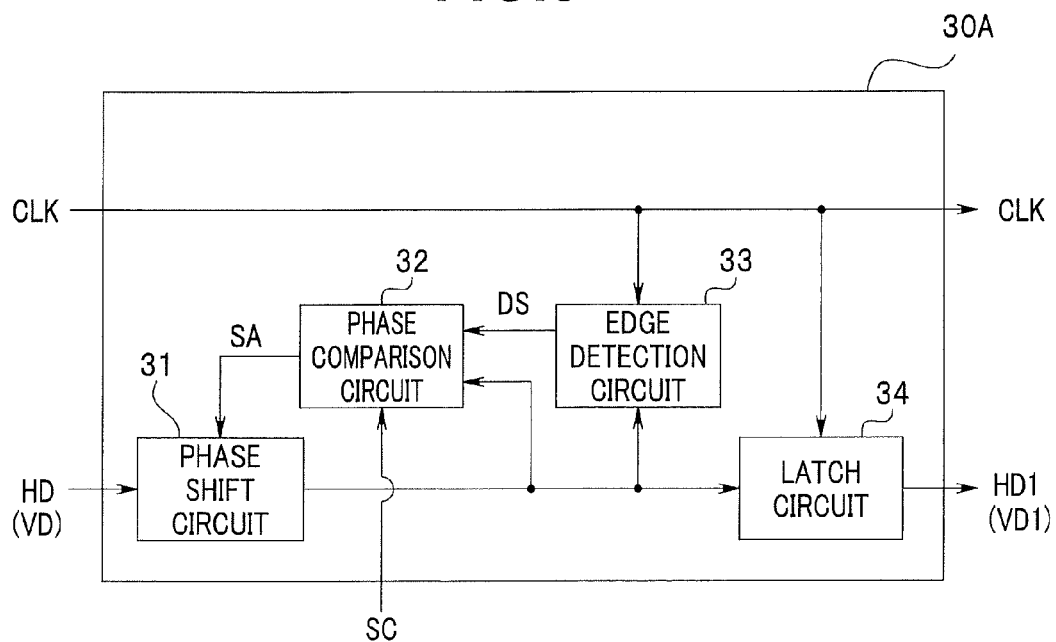
FIG. 3 is a diagram illustrating another example of the out-of-synchronization prevention circuit in accordance with the embodiment of the present invention.

FIG. 2 and FIG. 3 are diagrams illustrating examples of circuits for preventing out-of-synchronization due to skew variations.

In order to properly transmit and receive data between the endoscope 2 and the main body portion 3, clock signals and the various signals based on clock signals are needed to be synchronized with each other, but if there is a skew variation, so-called out-of-synchronization occurs. For example, in a normal mode, a clock signal CLK and two synchronizing signals HD and VD are inputted to the endoscope 2, and in order to prevent out-of-synchronization caused by a skew variation between each synchronizing signal and a clock signal CLK, a circuit as shown in FIG. 2 or FIG. 3 is provided in the FPGA 13 of the endoscope 2.

FIG. 2 is an out-of-synchronization prevention circuit 30 for shifting clock signals CLK, and FIG. 3 is an out-of-synchronization prevention circuit 30A for shifting synchronizing signals HD. As shown in FIG. 2 and FIG. 3, each of the out-of-synchronization prevention circuits 30 and 30A includes a phase shift circuit 31, a phase comparison circuit 32, an edge detection circuit 33, and a latch circuit 34.

In FIG. 2, a clock signal CLK is inputted to the phase shift circuit 31, and a horizontal synchronizing signal HD is inputted to the latch circuit 34. The phase comparison circuit 32 compares output by the phase shift circuit 31 with output by the edge detection circuit 33. At the time of scanning, the phase comparison circuit 32 receives scan signals SC as input, and outputs shift amount signals SA according to the scan signals SC to the phase shift circuit 31. The phase comparison circuit 32 includes memory and outputs stored shift amount signals SA in a normal operation. The phase shift circuit 31 includes a programmable delay element and shifts a phase of clock signals CLK according to the inputted shift amount signals SA.

The edge detection circuit 33 is a circuit that detects output from the phase shift circuit 31 and an edge of horizontal synchronizing signals HD. At the time of scanning, the edge detection circuit 33 detects a timing of rising or falling of a clock signal CLK and a horizontal synchronizing signal HD as an edge, and supplies a detection signal DS to the phase comparison circuit 32.

Accordingly, at the time of scanning, the phase comparison circuit 32 shifts a clock signal CLK to store a shift amount signal SA with a largest margin of latch timing of a horizontal synchronizing signal HD, and outputs the stored shift amount signal SA in a normal operation.

The latch circuit 34 latches a horizontal synchronizing signal HD at a timing of a clock signal CLK1 that is phase-shifted in the phase shift circuit 31 and outputs a timing-adjusted horizontal synchronizing signal HD1. Thus, the out-of-synchronization prevention circuit 30 outputs the clock signal CLK1 that is phase-shifted based on the shift amount signal with the largest margin of latch timing and also outputs the horizontal synchronizing signal HD1 latched at the timing of the clock signal CLK1.

In FIG. 3, an inputted clock signal CLK is directly outputted, and a horizontal synchronizing signal HD is inputted to the phase shift circuit 31. In FIG. 2, while a phase of a clock signal CLK is shifted, in FIG. 3, at the time of scanning, a phase of a horizontal synchronizing signal HD is shifted.

The latch circuit 34 outputs the horizontal synchronizing signal HD1 that is phase-shifted and timing-adjusted in the phase shift circuit 31. Thus, the out-of-synchronization prevention circuit 30A outputs the horizontal synchronizing signal HD1 that is phase-shifted based on the shift amount signal with the largest margin of latch timing, and also outputs a clock signal CLK.

As hereinbefore discussed, according to the out-of-synchronization prevention circuits 30 and 30A, out-of-synchronization due to skew variations can be prevented. The example described above is to prevent out-of-synchronization between a clock signal CLK and a horizontal synchronizing signal HD, but in order to prevent out-of-synchronization between a clock signal CLK and a vertical synchronizing signal VD, the similar circuits are provided. Furthermore, to prevent out-of-synchronization between other clock signals and other signals, the similar circuits as those in FIG. 2 and FIG. 3 are applicable.

(Operation)

Next, an operation of the endoscope apparatus 1 will be described.

(Observation Mode)

If a user observes a subject with the endoscope 2, the user operates the operation portion of the main body portion 3 to set the main body portion 3 to the observation mode. As described above, in the observation mode, according to mode switching signals SW, the switches of the switch groups 15 and 24 select the a-side.

Accordingly, the CCD 11 is driven based on a clock signal CLK, a horizontal synchronizing signal HD, a vertical synchronizing signal VD, and a control signal TX from the FPGA 22 of the main body portion 3. Image signals IM of a subject image from the CCD 11 are supplied to the image processing unit 21 of the main body portion 3 via the signal line 5f, and the image of the subject is displayed on the monitor 4. As a result, the user is allowed to observe the subject.

(Data Writing Mode and Unit Test Mode)

If new data is written in the flash memory 14 of the endoscope 2 and if units in the endoscope are tested, the user operates the operation portion of the main body portion 3 to set the main body portion 3 to any one of the modes. Data to be written in the flash memory 14 includes, as described above, the configuration data and the setting data. New data is written in the flash memory 14 if the endoscope 2 is upgraded.

For example, if data is written in the flash memory 14 of the endoscope 2 or if units in the endoscope are tested, the user connects the PC 6 to the main body portion 2 through the connector 3a. Configuration data for a new configuration of the FPGA 13 is stored in a storage apparatus of the PC 6 in advance. The user operates a keyboard or the like of the PC 6 to make an instruction to write data in the flash memory 14 or to perform processing of a unit test. In response to the instruction, the PC 6 executes processing shown in FIG. 4. As described above, writing data in the flash memory 14 and the unit test are performed using the JTAG function.

Figure 4:
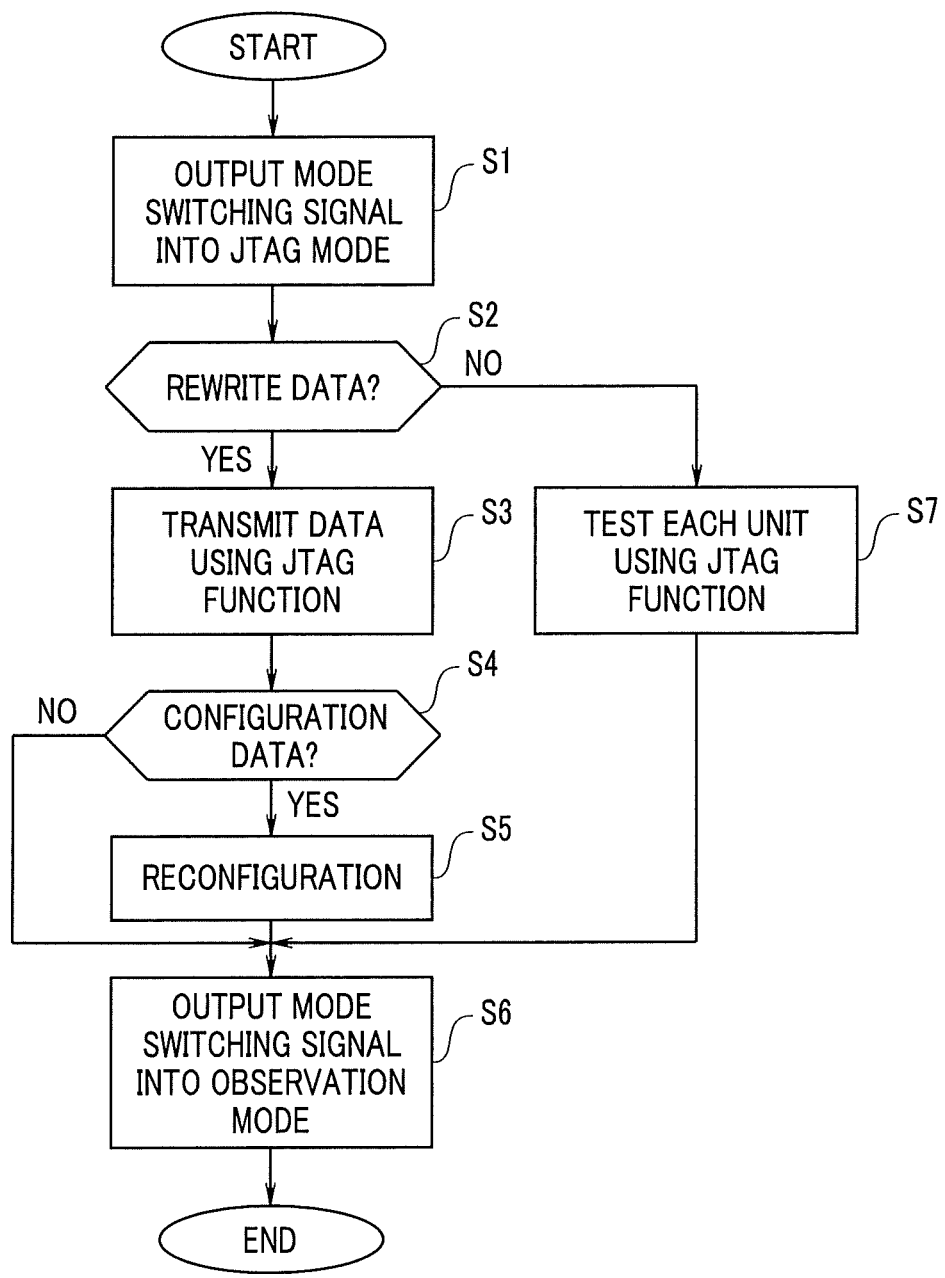
FIG. 4 is a flow chart illustrating an example of a flow of processing performed by a PC 6 at the time of writing data in a flash memory 14 and a unit test for an endoscope in accordance with the embodiment of the present invention.

FIG. 4 is a flow chart showing an example of a flow of processing performed by the PC 6 at the time of writing data in the flash memory 14 and a unit test for the endoscope.

Once being instructed by the user to rewrite data or perform a unit test, the PC 6 outputs a mode switching signal SW for switching to a JTAG mode (S1). The mode switching signal SW is outputted and supplied to each switch through the I/O portion 23, so that each switch switches to the b-side. As a result, the endoscope 2 enters into the JTAG mode.

Next, it is determined whether or not the user's instruction is to rewrite data (S2).

If the instruction is to rewrite data (S2: YES), the PC 6 transmits data stored in the storage apparatus using the JTAG function (S3).

Once the data transmission is ended, the PC 6 determines whether or not the transmitted data is configuration data (S4).

If the transmitted data is configuration data (S4: YES), the PC 6 outputs a reset signal to the endoscope 2 to reconfigure the FPGA 13 (S5). Receiving the reset signal, the endoscope 2 is reactivated, and the FPGA 13 is configured by reading in new configuration data from the flash memory 14.

Then, once the reconfiguration is ended, the PC 6 outputs a mode switching signal SW for switching the JTAG mode to the observation mode (S6), and then the processing is ended.

If NO in S4, then the processing proceeds to S6. In this manner, since the FPGA 13 is automatically reconfigured after configuration data is rewritten, the user is allowed to observe the subject in the observation mode immediately after the endoscope 2 is upgraded. If the instruction is not to rewrite configuration data (S2: NO), the PC 6 tests each unit using the JTAG function (S7). The PC 6 tests which of the unit including the flash memory 14 and the unit including the FPGA 13 is out of order, and if there is an abnormality, an abnormal unit is detected.

As described above, the CCD 11 and the AFE 12 may be included in the chain of JTAG as well as circuits in the operation portion, not shown, may also be included in the chain of JTAG. In this way, by testing each circuit in the endoscope 2 with JTAG, units in each circuit can be tested for each unit. For a unit having a detected abnormality, measures such as replacing the unit can be taken.

If the process of S7 is ended, then the processing proceeds to S6, and the PC 6 terminates the processing.

Therefore, according to the above configuration, an endoscope and an endoscope apparatus may be provided which can reduce the number of signal lines in a cable for connecting the endoscope and a main body portion to each other.

Conventionally, in the case of an endoscope apparatus having a plurality of modes, since a plurality of dedicated lines needed for modes other than a normal observation mode are provided in a cable between an endoscope and a main body portion, disadvantageously, the number of signal lines in the cable has been large.

For example, a vertical synchronizing signal line, a horizontal synchronizing signal line, a signal line for transmitting/receiving data, and an image signal line are needed for the normal observation mode. Furthermore, as dedicated lines for the mode in which data is written in a memory of an endoscope, a data line, a clock line, a control signal line for transmission/reception, and the like are needed. Providing these dedicated lines in the cable between the endoscope and the main body portion has caused a complicated entire configuration of the endoscope apparatus and an increase in cost.

Also, in some endoscope apparatuses, data is written in a memory in an endoscope using a connector that is provided in the endoscope itself, for connecting with an external device, without using a signal line in a cable with a main body portion. However, if the endoscope itself is provided with a dedicated connector, there arises another problem that a variety of constitutional measures must be taken to strength of the endoscope itself, watertightness for an autoclave, etc.

As hereinbefore discussed, according to the endoscope apparatus of the present embodiment described above, since the number of signal lines in a cable that connects an endoscope and a main body portion to each other can be reduced, a diameter of the cable can also be reduced.

Further, if the FPGA 13, the flash memory 14, the switch group 15, and the like are installed in a distal end portion of an insertion portion, a diameter of the insertion portion of the endoscope can be reduced. For example, if the analog front end portion 12, the FPGA 13, the flash memory 14 and the switches 15*a* to 15*e* are implemented in one chip which is provided in a distal end portion of the insertion portion of the endoscope 2, reducing a diameter of the insertion portion of the endoscope 2 can be achieved.

In the description made hereinbefore, data is written in the endoscope using the JTAG standard, which is one of debugging serial interfaces, but data may be written with data communications that use a protocol other than the JTAG standard.

The present invention is not limited to the aforementioned embodiment, and a variety of variations and modifications can be made without changing the gist of the present invention.

What is claimed is:

1. An endoscope connectable to an outside apparatus, the endoscope comprising:
   an image pickup device that picks up an image of a subject;
   an image pickup control portion that is controlled by the outside apparatus to output a drive signal for driving the image pickup device and transmits an image pickup signal outputted from the image pickup device to the outside apparatus;
   a rewritable storage portion in which at least one of program data and setting data that relate to an operation of the image pickup control portion is stored; and
   a switching control portion that, based on a rewriting instruction signal of the at least one data in the storage portion, switches so that the at least one data received by using all or a part of signal lines for the image pickup device, the lines being provided to connect the outside apparatus to the endoscope and associated with observation of the subject, is inputted to the storage portion.

2. The endoscope according to claim 1, wherein
   the image pickup control portion is a programmable device, an internal configuration of which is changeable based on configuration data, and
   the at least one data includes the configuration data.

3. The endoscope according to claim 1, wherein
   the image pickup control portion and the storage portion are connected to a debugging serial interface, and
   writing the at least one data into the storage portion is performed using the debugging serial interface.

4. The endoscope according to claim 1, wherein
   the switching control portion includes a plurality of switches that, when the switching control portion receives the rewriting instruction signal, switch connection to the image pickup control portion, of all or a part of the signal lines associated with the observation, to connection to the storage portion.

5. An endoscope apparatus including an outside apparatus and an endoscope connectable to the outside apparatus via a cable, wherein
   the endoscope comprises:
   an image pickup device that picks up an image of a subject;
   an image pickup control portion that is controlled by the outside apparatus to output a drive signal for driving the image pickup device and transmits a signal obtained by processing an image pickup signal outputted from the image pickup device to the outside apparatus;
   a rewritable storage portion in which at least one of program data and setting data that relate to an operation of the image pickup control portion is stored; and
   a switching control portion that, based on a rewriting instruction signal of the at least one data in the storage portion, switches so that the at least one data received by using all or a part of signal lines included in the cable for the image pickup device, the lines being associated with observation of the subject, is inputted to the storage portion.

6. The endoscope apparatus according to claim 5, wherein
   the image pickup control portion is a programmable device, an internal configuration of which is changeable based on configuration data, and
   the at least one data includes the configuration data.

7. The endoscope apparatus according to claim 6, wherein
   the outside apparatus writes the configuration data into the storage portion, thereafter reconfiguring the image pickup control portion so as to change the internal configuration of the image pickup control portion based on the written configuration data.

8. The endoscope apparatus according to claim 5, wherein
   the outside apparatus, the image pickup control portion and the storage portion are connected to each other through a debugging serial interface, and
   writing the at least one data into the storage portion is performed using the debugging serial interface from the outside apparatus.

9. The endoscope apparatus according to claim 5, wherein
   the switching control portion includes a plurality of switches that, when the switching control portion receives the rewriting instruction signal, switch connection to the image pickup control portion, of the signal lines associated with the observation, to connection to the storage portion.

10. The endoscope apparatus according to claim 9, wherein
the cable includes a signal line for the rewriting instruction signal, and
the plurality of switches perform switching of the connection according to the rewriting instruction signal from the signal line for the rewriting instruction signal.

11. The endoscope apparatus according to claim 5, wherein
the cable includes a signal line for the image pickup signal outputted from the image pickup device.

* * * * *